(12) United States Patent
Sasaki et al.

(10) Patent No.: US 10,502,558 B2
(45) Date of Patent: Dec. 10, 2019

(54) CURVATURE SENSOR

(71) Applicant: OLYMPUS CORPORATION, Tokyo (JP)

(72) Inventors: Yasuo Sasaki, Machida (JP); Eiji Yamamoto, Musashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/983,172

(22) Filed: May 18, 2018

(65) Prior Publication Data
US 2018/0266812 A1    Sep. 20, 2018

Related U.S. Application Data

(63) Continuation of application No. PCT/JP2015/082753, filed on Nov. 20, 2015.

(51) Int. Cl.
*G01B 11/255*    (2006.01)
*G01B 11/24*     (2006.01)
(Continued)

(52) U.S. Cl.
CPC ........ *G01B 11/255* (2013.01); *A61B 1/00165* (2013.01); *G01B 11/18* (2013.01);
(Continued)

(58) Field of Classification Search
CPC ....... G01B 11/255; G01B 11/18; G01B 11/24; A61B 1/00165; G02B 6/02042; G02B 6/022; G02B 6/034
See application file for complete search history.

(56) References Cited

U.S. PATENT DOCUMENTS 5,563,967 A * 10/1996 Haake .................... G01B 11/18
                                                                250/227.14
6,256,090 B1    7/2001 Chen et al.
(Continued)

FOREIGN PATENT DOCUMENTS

JP      2000-258190 A      9/2000
JP      2001-516011 A      9/2001
(Continued)

OTHER PUBLICATIONS

English translation of International Preliminary Report on Patentability dated May 31, 2018 together with the Written Opinion received in related International Application No. PCT/JP2015/082753.
(Continued)

*Primary Examiner* — Dominic J Bologna
(74) *Attorney, Agent, or Firm* — Scully, Scott, Murphy & Presser, P.C.

(57) ABSTRACT

A curvature sensor includes a light source, a flexible light guide including cores, FBG sensors that are provided in the cores and constitute FBG sensor groups at predetermined positions along longitudinal axes of the cores. The curvature sensor includes a detector that detects an optical spectrum of light from the FBG sensors, and a processor that determines a bend position and a bend amount of the light guide. The FBG sensor groups include a first FBG sensor group and a second FBG sensor group next to it. FBG sensors in the first and second FBG sensor groups include gratings having first and second pitches. The first pitch is shorter than the second pitch and is closer to the second pitch than other pitches of gratings of FBG sensors that include gratings having pitches shorter than the second pitch.

9 Claims, 11 Drawing Sheets

(51) Int. Cl.
*A61B 1/00* (2006.01)
*G02B 6/34* (2006.01)
*G01B 11/16* (2006.01)
*G02B 6/02* (2006.01)

(52) U.S. Cl.
CPC .............. *G01B 11/24* (2013.01); *G02B 6/34* (2013.01); *G02B 6/022* (2013.01); *G02B 6/02042* (2013.01); *G02B 6/02076* (2013.01)

(56) References Cited

U.S. PATENT DOCUMENTS

| | | | |
|---|---|---|---|
| 6,492,636 B1 | 12/2002 | Chen et al. | |
| 7,781,724 B2 | 8/2010 | Childers et al. | |
| 2010/0080502 A1* | 4/2010 | Nishikawa | G01N 21/774 |
| | | | 385/12 |
| 2010/0215311 A1* | 8/2010 | Moore | G01B 11/18 |
| | | | 385/13 |
| 2011/0098533 A1* | 4/2011 | Onoda | A61B 1/0051 |
| | | | 600/117 |
| 2015/0313503 A1* | 11/2015 | Seibel | A61B 1/00165 |
| | | | 600/103 |

FOREIGN PATENT DOCUMENTS

| | | |
|---|---|---|
| JP | 2006-172339 A | 6/2006 |
| JP | 2006-284494 A | 10/2006 |
| JP | 2010-104427 A | 5/2010 |
| JP | 2014-226319 A | 12/2014 |

OTHER PUBLICATIONS

International Search Report dated Jan. 12, 2016 issued in PCT/JP2015/082753.

Japanese Office Action dated Apr. 16, 2019 in Japanese Patent Application No. 2017-551503.

* cited by examiner

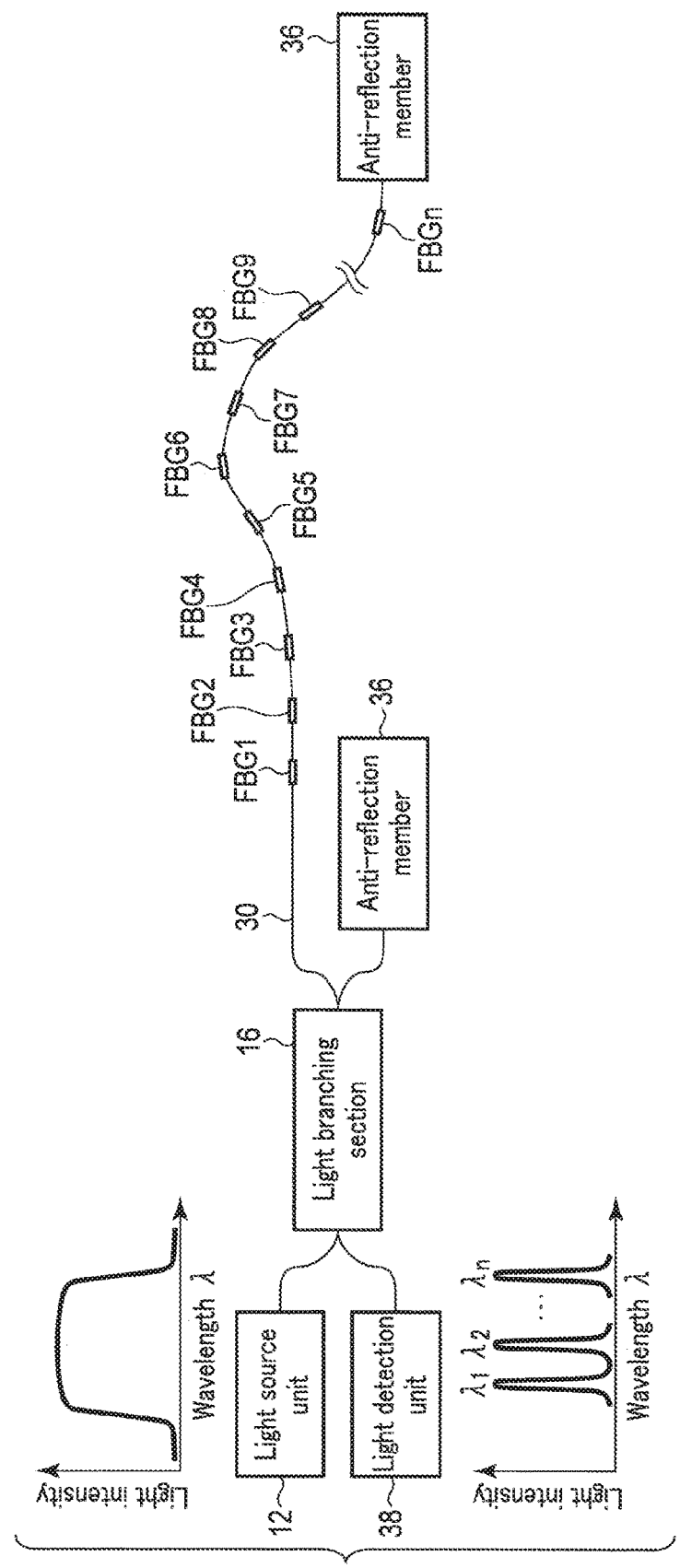
F I G. 9

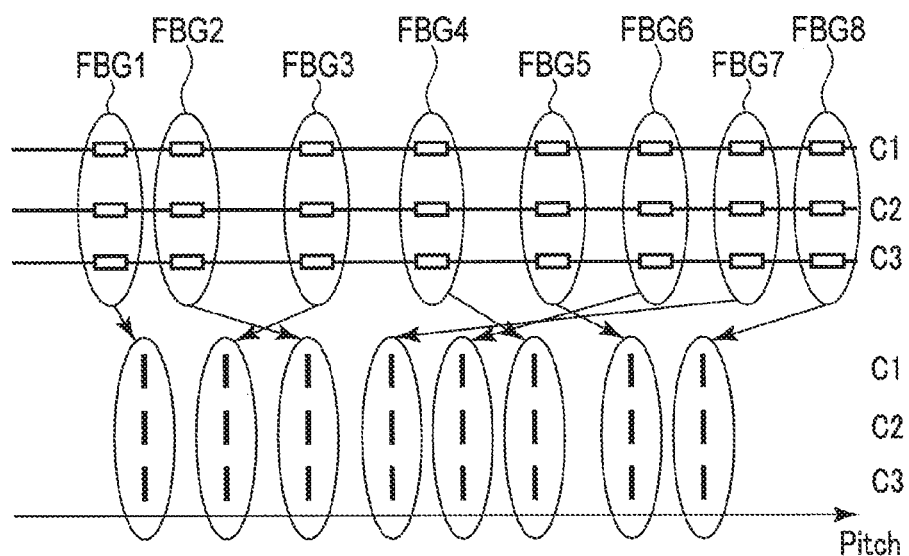
F I G. 15

CURVATURE SENSOR

CROSS-REFERENCE TO RELATED APPLICATIONS

This application is a Continuation Application of PCT Application No. PCT/JP2015/082753, filed Nov. 20, 2015, the entire contents of which are incorporated herein by reference.

BACKGROUND OF THE INVENTION

1. Field of the Invention

The present invention relates to a curvature sensor that determines a bend of a measurement object.

2. Description of the Related Art

U.S. Pat. No. 6,256,090 discloses a technique of measuring a shape of an elongated flexible body by using four or five fibers provided with fiber Bragg grating (FBG) sensors. The four or five fibers are arranged around the flexible body. Three fibers are used for measurement of the shape of the flexible body based on a difference in response of each FBG sensor with respect to a change in shape of the flexible body. One fiber is used for temperature change correction. One fiber is used for twist correction.

U.S. Pat. No. 7,781,724 discloses a technique of measuring a shape of a flexible body by using three (two or more) cores provided with FBG sensors. The three cores are, in an example, cores of multicore fibers, and in another example, cores of single core fibers of a fiber bundle. An optical signal from each of three FBG sensors in each group is separated by a frequency domain reflectometer. The shape of the fiber or fiber bundle is determined by obtaining a bend amount of each portion of the fiber or fiber bundle from strain of each of the three FBG sensors in each group to integrate the bend amount of each portion.

BRIEF SUMMARY OF THE INVENTION

A curvature sensor includes a light source that emits light, a flexible light guide including cores that are disposed so as to maintain relative spaces and guide light emitted from the light source, FBG sensors that are provided in the respective cores of the light guide and constitute FBG sensor groups at predetermined positions along longitudinal axes of the cores, respectively. Each FBG sensor includes a grating having a predetermined pitch and reflects light with a particular wavelength in light guided by the cores. The curvature sensor also includes a detector that detects information on an optical spectrum of light reflected by the FBG sensors or light passing through the FBG sensors, and a processor that determines a bend position and a bend amount of the light guide based on the information on an optical spectrum. The FBG sensor groups positioned at the predetermined positions include a first FBG sensor group and a second FBG sensor group that is provided next to the first FBG sensor group in a longitudinal direction of the light guide. All FBG sensors included in the first FBG sensor group each include a first grating having a predetermined first pitch, all FBG sensors included in the second FBG sensor group each include a second grating having a predetermined second pitch. The first pitch is shorter than the second pitch, and the first pitch is closer to the second pitch than other pitches of gratings of FBG sensors in all FBG sensor groups that include gratings having pitches shorter than the second pitch.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 shows an optical system of the curvature sensor shown in FIG. 1.

FIG. 15 shows another example of a positional relationship among the FBG sensor groups along a length of the cores and a relative relationship among pitches of the FBG sensors in each FBG sensor group in a pitch space.

DETAILED DESCRIPTION OF THE INVENTION

Figure 1:
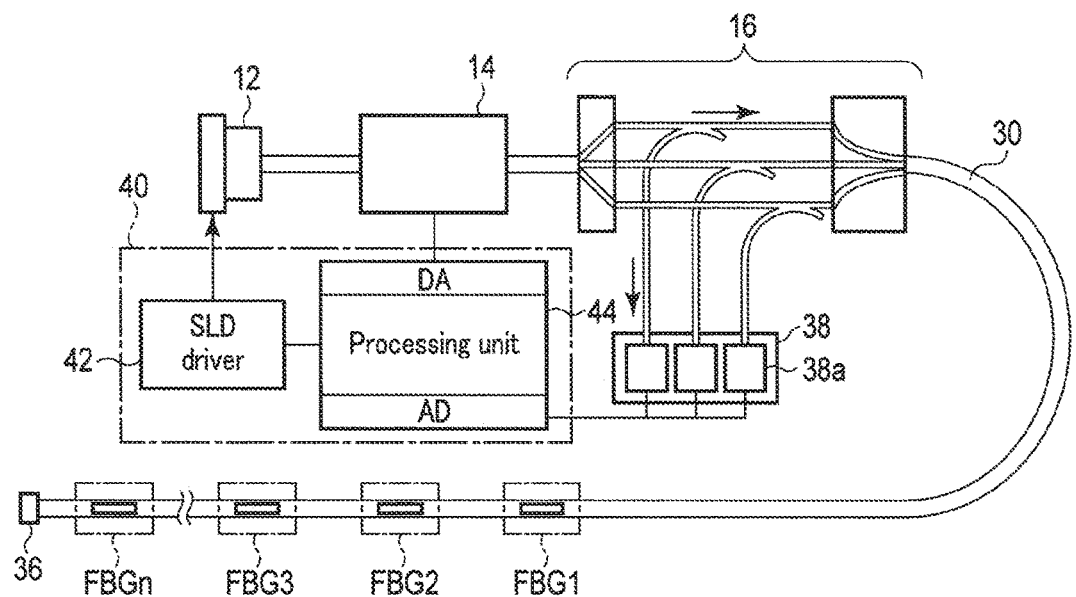
FIG. 1 shows a curvature sensor according to an embodiment.

FIG. 1 shows a curvature sensor according to an embodiment. The curvature sensor comprises an elongated flexible light guide 30 including a plurality of cores, for example three cores, a light source unit 12 that emits light to be guided by the light guide 30, a spectroscopic unit 14 that spectrally disperses the light from the light source unit 12, and a light branching section 16 that distributes the light from the spectroscopic unit 14 to cores of light guide 30. Respective light sources may be provided for individual cores of the light guide 30, in which case the leftmost element in the light branching section 16 is unnecessary.

The light source unit 12 may be constituted by a continuous light source that emits light having a broadband spectrum, such as a super luminescent diode (SLD).

The spectroscopic unit 14 may be constituted by a wavelength selectable optical system, such as a tunable filter. The spectroscopic unit 14 has a function of producing light having a narrow band spectrum from light having a broadband spectrum from the light source unit 12. The spectroscopic unit 14 also has a function of wavelength sweeping.

The light guide 30 has fiber Bragg grating sensor groups FBG1, FBG2, FBG3, ..., and FBGn. Hereinafter, the fiber Bragg grating sensor groups FBG1, FBG2, FBG3, ..., and FBGn are simply abbreviated to the FBG sensor groups.

Figure 2:
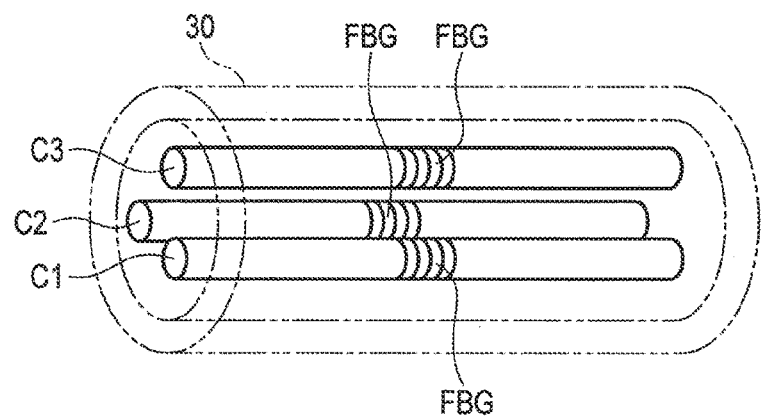
FIG. 2 schematically shows an FBG sensor group shown in FIG. 1.

FIG. 2 schematically shows an FBG sensor group. The cores C1, C2, and C3 of the light guide 30 extend along the length of the light guide 30 while maintaining relative spaces. That is, a relative position of the cores C1, C2, and C3 on a plane perpendicular to an axis of the light guide 30 is kept unchanged. In FIG. 2, the cores C1, C2, and C3 are drawn so as to extend straight and in parallel to one another, but it is not limited thereto, for example, the cores may extend while twisting in a toroidal shape.

Each FBG sensor group includes fiber Bragg grating sensors FBGs provided in each of the cores C1, C2, and C3 of the light guide 30. Hereinafter, a fiber Bragg grating sensor FBG is abbreviated to an FBG sensor. For example, in each FBG sensor group, one FBG sensor is provided for each of the cores C1, C2, and C3. That is, each FBG sensor group includes the same number of FBG sensors as the number of the cores C1, C2, and C3, that is, three FBG sensors. The three FBG sensors in each FBG sensor group are formed so as to be partially overlapped with one another in the length along the axes of the cores C1, C2, and C3.

Each FBG sensor is constituted by a grating in which a refractive index periodically changes in a longitudinal direction of each of the cores C1, C2, and C3. When light enters an FBG sensor, only components of a specific wavelength $\Delta_B = 2n\Lambda$ interfere so as to be intensified. Here, $\Delta_B$ is a Bragg wavelength, n is a refractive index of a core, and $\Lambda$ is a pitch (period) of a grating. As a result, the FBG sensor reflects only the components of the specific wavelength of light, and transmits components of the other wavelengths.

The FBG sensors formed in the respective cores C1, C2, and C3 along their axes have mutually different pitches. Therefore, the wavelengths of light reflected respectively by the FBG sensors formed in the respective cores C1, C2, and C3 are different from one another.

In FIG. 2, the light guide 30 is drawn as a multicore fiber, but it is not limited thereto, and the light guide 30 may be constituted by a plurality of fibers provided with FBG sensors. In this case, at least portions of the FBG sensors need to be adhesively fixed so that mutual spaces will not change.

As shown in FIG. 1, the light guide 30 is preferably provided with an anti-reflection member 36 at the end. The light branching section 16 branches light returned from the FBG sensors to extract and output the branched light. The curvature sensor also comprises a light detection unit 38 including light detectors 38a that detect return light outputted from the light branching section 16, and a processing unit 44 that determines a bend of the light guide 30 based on information on a spectrum of the detected return light from the FBG sensors. The processing unit 44 also includes an SLD driver 42 that drives the light source unit 12 and has a function of controlling the spectroscopic unit 14.

(Calculation Method of Curvature Radius and Direction)

When a portion of the light guide 30 in which an FBG sensor group is located is bent, FBG sensors in the FBG sensor group extend differently with respect to the bend of the light guide 30. As a result, the FBG sensors in the FBG sensor group show different responses. That is, since a core located on an outer side of a center axis of the light guide 30 extends, the FBG sensor formed in the core also extends in the same manner, so that a pitch of the FBG sensor increases. As a result, a Bragg wavelength becomes long. That is, a wavelength of light reflected by the FBG sensor becomes long. On the contrary, since a core located on an inner side of the center axis of the light guide 30 contracts, the FBG formed in the core also contracts, so that a pitch of the FBG sensor decreases. As a result, a Bragg wavelength becomes short. That is, a wavelength of light reflected by the FBG sensor becomes short. By measuring changes in Bragg wavelength of FBG sensors in an FBG sensor group, it is possible to determine in what direction the portion of the light guide 30 where the FBG sensor group is located is bent and to what degree it is bent.

Figure 3:
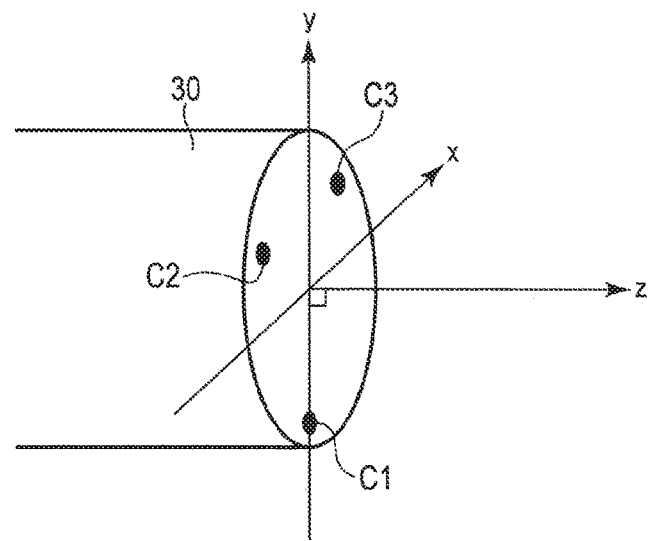
FIG. 3 is a view for explaining a principle of obtaining a bend of a light guide shown in FIG. 1, and shows a setting of a coordinate system for the light guide.
Figure 4:
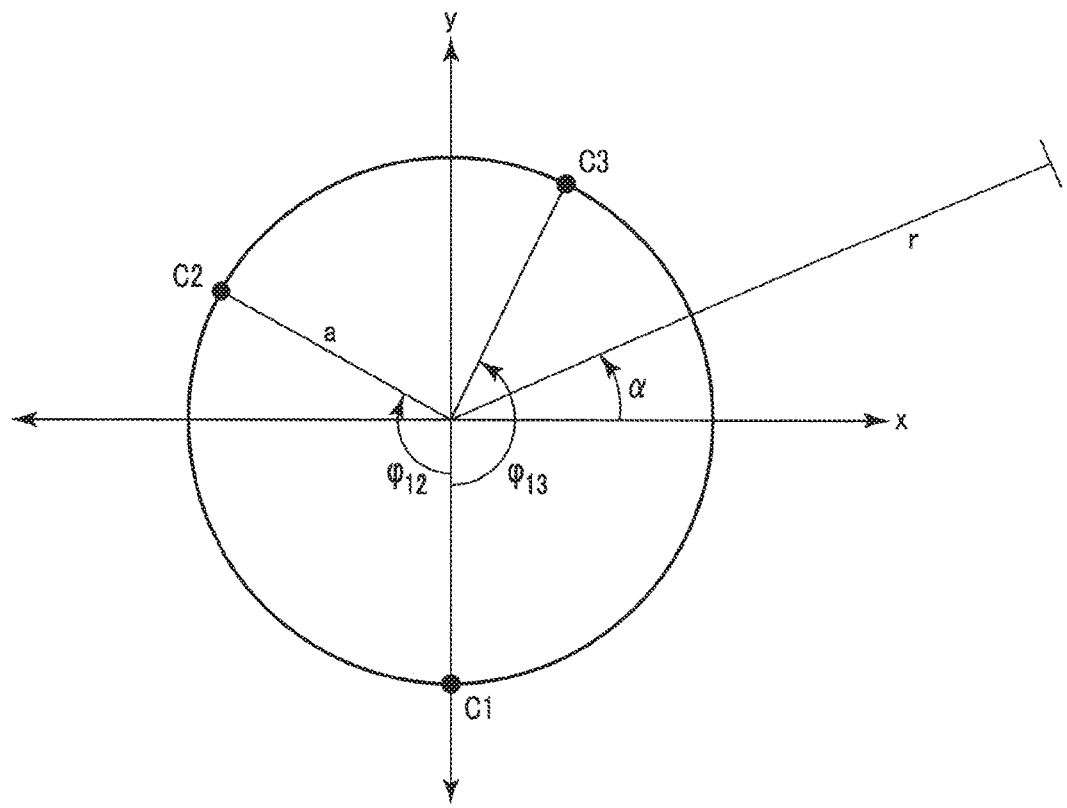
FIG. 4 is a view for explaining a principle of obtaining a bend of the light guide shown in FIG. 1, and shows a relative positional relationship between a bending direction of the light guide and three cores.
Figure 5:
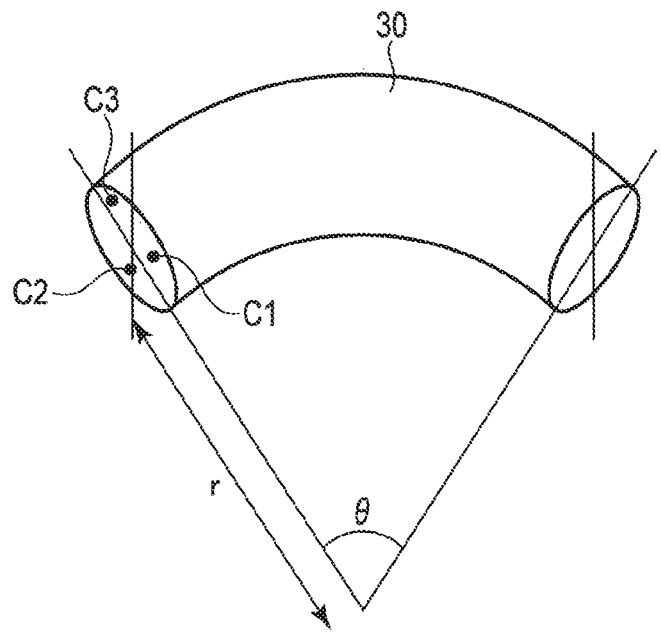
FIG. 5 is a view for explaining a principle of obtaining a bend of the light guide shown in FIG. 1, and shows the bent light guide.
Figure 6:
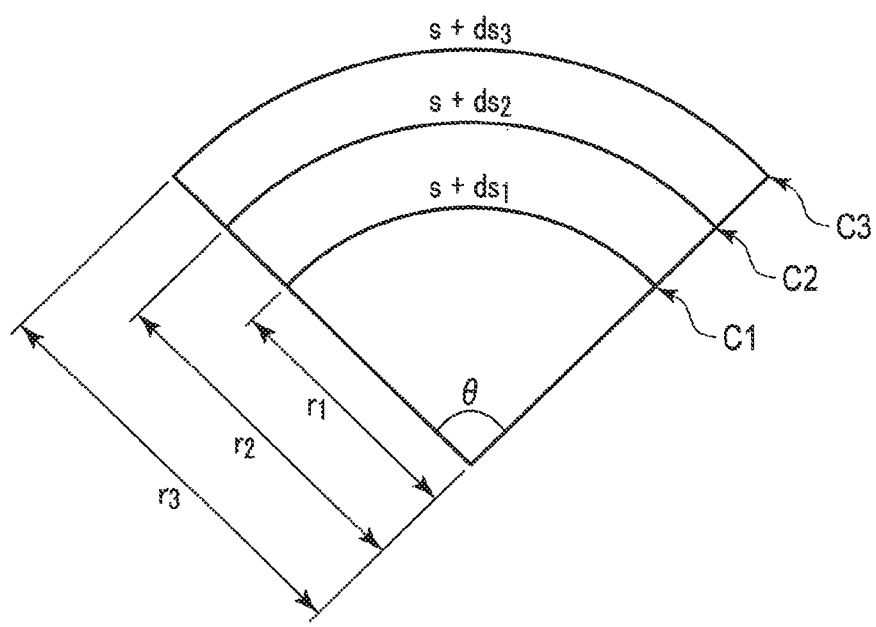
FIG. 6 is a view for explaining a principle of obtaining a bend of the light guide shown in FIG. 1, and schematically shows bends of the three cores.

Hereinafter, a principle of obtaining a bend of the light guide 30 will be described with reference to FIGS. 3 to 7. As shown in FIG. 3, it is assumed that a direction in which the cores C1, C2, and C3 extend is a z axis, and, with the center of the FBG sensor group as an origin, a direction from the origin toward the core C1 is a y axis. As shown in FIGS. 4 and 5, it is assumed that the light guide 30 is bent in a direction of an angle α from the x axis at a curvature radius r. Extensions of the respective cores C1, C2, and C3 with respect to an angle θ can be represented as $s+ds_1$, $s+ds_2$, and $s+ds_3$, where s is an extension of an origin, as shown in FIG. 6. A relationship among them is represented by the following Equation (1) using curvature radii $r_1$, $r_2$, and $r_3$ of the respective cores shown in FIG. 7:

$$\theta = \frac{s+ds_1}{r_1} = \frac{s+ds_2}{r_2} = \frac{s+ds_3}{r_3} \tag{1}$$

If this is modified and strain of each core is defined as $\varepsilon_i = ds_i/s$, the above Equation (1) results in the following Equation (2):

$$\frac{1+\varepsilon_1}{r_1} = \frac{1+\varepsilon_2}{r_2} = \frac{1+\varepsilon_3}{r_3} \tag{2}$$

Figure 7:
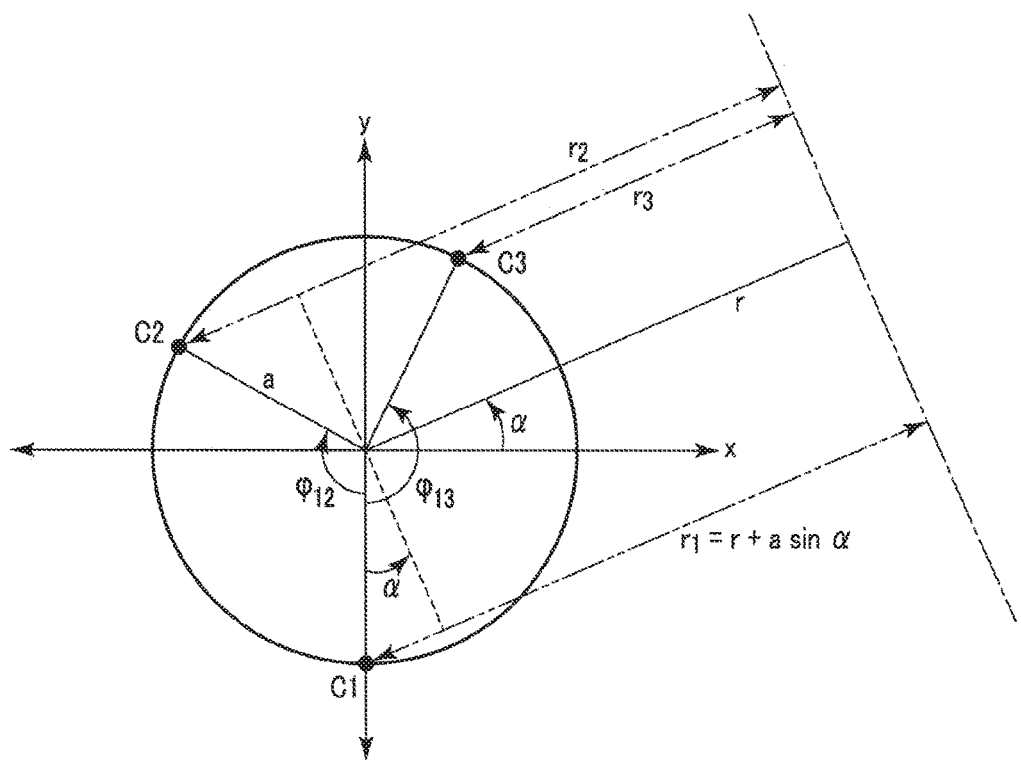
FIG. 7 is a view for explaining a principle of obtaining a bend of the light guide shown in FIG. 1, and shows a relative positional relationship and curvature radii of the bends of the three cores.

From FIG. 7, the curvature radii $r_1$, $r_2$, and $r_3$ of the respective cores are represented by the following Equation (3):

$$r_1 = r + a \sin \alpha$$

$$r_2 = r + a \sin(\alpha - \varphi_{12})$$

$$r_3 = r + a \sin(\alpha - \varphi_{13}) \tag{3}$$

Therefore, the relationship of the following Equation (4) results:

$$(1+\varepsilon_1)(r+a\sin(\alpha-\varphi_{12}))=(1+\varepsilon_2)(r+a\sin(\alpha))$$

$$(1+\varepsilon_1)(r+a\sin(\alpha-\varphi_{13}))\times(1+\varepsilon_3)(r+a\sin(\alpha))$$

$$(1+\varepsilon_2)(r+a\sin(\alpha-\varphi_{13}))\times(1+\varepsilon_3)(r+a\sin(\alpha-\varphi_{12})) \quad (4)$$

Here, parameters are replaced as indicated in the following Equation (5):

$$\varepsilon_{12}=\varepsilon_2-\varepsilon_1 \; \varepsilon_{13}=\varepsilon_3-\varepsilon_1 \; \varepsilon_{23}=\varepsilon_3-\varepsilon_2$$

$$\sigma_1=1+\varepsilon_1 \; \sigma_2=1+\varepsilon_2 \; \sigma_3=1+\varepsilon_3 \quad (5)$$

Then, $\alpha$ is represented by the following Equation (6), and $r$ is represented by the following Equation (7):

$$\tan\alpha = \frac{\varepsilon_{13}\sin\varphi_{12} + \varepsilon_{12}\sin\varphi_{13}}{\varepsilon_{23} - \varepsilon_{13}\cos\varphi_{12} - \varepsilon_{12}\cos\varphi_{13}} \quad (6)$$

$$r = \begin{cases} \dfrac{a}{\varepsilon_{12}}(\sigma_1\sin(\alpha+\varphi_{12}) - \sigma_2\sin(\alpha)) \\ \dfrac{a}{\varepsilon_{13}}(\sigma_1\sin(\alpha+\varphi_{13}) - \sigma_3\sin(\alpha)) \\ \dfrac{a}{\varepsilon_{23}}(\sigma_2\sin(\alpha-\varphi_{13}) - \sigma_3\sin(\alpha+\varphi_{12})) \end{cases} \quad (7)$$

Therefore, it can be seen that $r$ and $\alpha$ can be obtained from strain differences $\varepsilon_{12}$, $\varepsilon_{13}$, and $\varepsilon_{23}$ of the three FBG sensors.

As a matter of course, by similar derivation, $r$ and $a$ can be obtained based on two FBG sensors. However, when being based on three FBG sensors, even in a case where all the FBG sensors uniformly extend due to reasons other than bending, such as temperature and pulling, their effects can cancel out one another. Therefore, a derivation example based on three FBG sensors is presented here.

In a case where the bending is restricted within a two-dimensional plane, a curvature radius of the bend can be obtained from a difference between strains of two FBG sensors by using two cores like the above consideration.

Similarly to the above annotation, a curvature radius can be obtained based on one FBG sensor, but taking into consideration the effect of canceling in the case of the FBG sensors extending uniformly, it is desirable to obtain a curvature radius based on the two FBG sensors.

By performing such bending detection at several positions, it is possible to calculate the shape by integrating a bend amount at each position. For example, it is possible to obtain information on what kind of shape a colonoscope has in the body.

Figure 8:
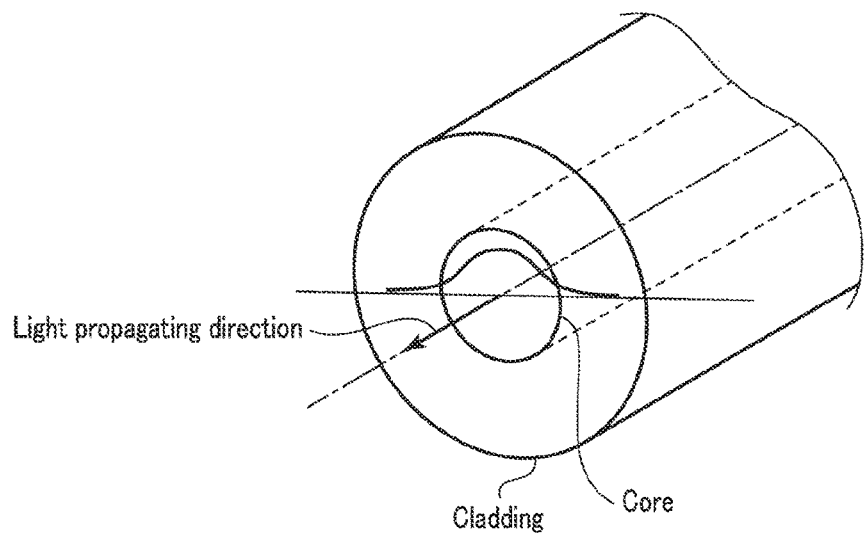
FIG. 8 shows seeping of light propagating along a core into a cladding.

(Relationship Between Pitch and Bragg Wavelength) In single mode fibers, the number of modes of light passing through a core is one. A Bragg reflection wavelength $\lambda_B$ with respect to a pitch $\Lambda$ of an FBG sensor is determined by $\lambda_B=2n\Lambda$ (n is a refractive index), as described above. The refractive index n is close to the refractive index of the core, but since the light propagating along the core involves seeping into a cladding as shown in FIG. 8, the refractive index n is an effective refractive index, which is also influenced by the cladding. The extent of the influence of the cladding depends on the amount of seeping into the cladding based on the size of core diameter. Also, since a refractive index of each core of a multicore fiber varies according to characteristics of each core, such as a doping amount of Ge, their Bragg reflection wavelengths are not necessarily the same even if they have the same pitch. However, if the cores have the same diameter and the same characteristics, the cores would have the same Bragg reflection wavelength when FBG sensors with the same pitch are formed in the multicore.

(Optical System)

In FIG. 1, light having a broadband spectrum emitted from the light source unit 12 is spectrally dispersed by the spectroscopic unit 14 to be converted into light having a narrowband spectrum and also be wavelength swept. The light from the spectroscopic unit 14 is branched by the light branching section 16, and then introduced into the three cores C1, C2, and C3 of the light guide 30. The light guided by the light guide 30 is reflected by the FBG sensor groups, and then returns to the light branching section 16. Return light from the respective cores C1, C2, and C3 is outputted from the light branching section 16, and is detected by the light detection unit 38. Thereby, an optical spectrum (a graph of light intensity relative to wavelength) is obtained.

The optical system may be modified so that, instead of the light source unit 12 that is a continuous light source, the light source unit 12 is constituted by a variable wavelength light source, such as a tunable laser, and the spectroscopic unit 14 that is a wavelength selectable optical system is omitted. Also, instead of the light entering the light guide 30 being spectrally dispersed, the return light may be spectrally dispersed by a wavelength selectable optical system, such as a tunable filter. When the return light is spectrally dispersed, the spectroscopic unit 14 is omitted, and light having a broadband spectrum emitted from the light source unit 12 is directly introduced into the three cores C1, C2, and C3 of the light guide 30.

FIG. 9 shows an optical system of the curvature sensor shown in FIG. 1. In FIG. 9, illustration of a spectroscopic unit is omitted. The light entering the light guide 30 is a wavelength-swept light, and has a broadband optical spectrum as shown in the upper left of FIG. 9. The optical spectrum of the return light from one of the cores of the light guide 30 has discrete peaks as shown in the lower left of FIG. 9. One peak corresponds to one FBG sensor.

Figure 10:
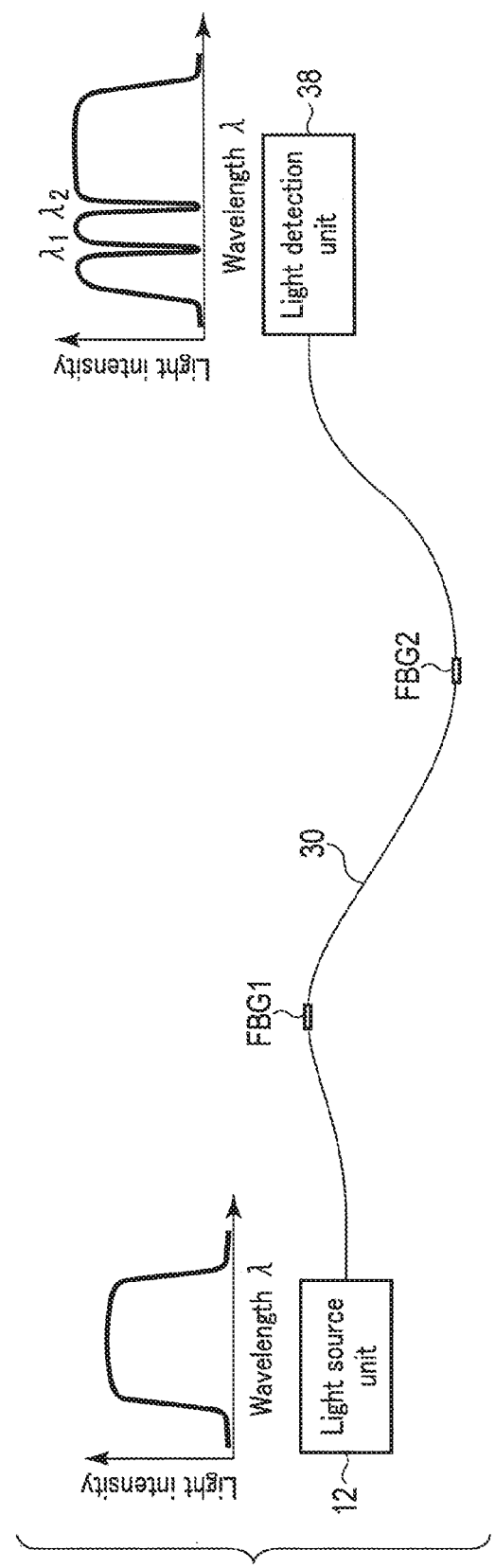
FIG. 10 shows an example of a transmission type optical system of a curvature sensor.

The optical system of the curvature sensor shown in FIG. 1 is constituted by a reflection type optical system, but may be constituted by a transmission type optical system instead. FIG. 10 shows an example of a transmission type optical system of a curvature sensor. Also in this figure, illustration of a spectroscopic unit is omitted. The spectroscopic unit may be provided at the subsequent stage of the light source unit 12 or at the front stage of the light detection unit 38. In addition, if the light source unit 12 is constituted by a tunable laser, etc., the spectroscopic unit may be omitted. The light entering the light guide 30 is a wavelength-swept light, and has a broadband optical spectrum as shown on the left side of FIG. 10. As shown on the right side of FIG. 10, an optical spectrum of a transmitted light passing through one of the cores of the light guide 30 has discrete dips. One dip corresponds to one FBG sensor.

As already described above, if the core is shifted from the center of the light guide 30, the optical spectrum obtained in the light detection unit 38 shows wavelength shifts of the peaks or dips according to the bend amount. From wavelength shifts of optical spectra of light from a plurality of cores, the bend amount of the light guide 30 in each FBG sensor portion can be calculated. By integrating the bend amount in each FBG sensor portion, the overall bend of the light guide 30, in other words, the shape of the light guide 30 can be calculated.

(General Selecting Manner of Wavelength Intervals of Adjacent FBG Sensors in Wavelength Space)

FBG sensors formed in a core are located in mutually different places along the axis of the core, and have mutually different pitches. That is, wavelengths of light respectively reflected by the FBG sensors on the core, that is, Bragg wavelengths are mutually different. Hereinafter, a wavelength of light reflected by an FBG sensor will be referred to as the Bragg wavelength of the FBG sensor, for the sake of convenience, although the FBG sensor does not have a Bragg wavelength. Thereby, position identification along the length of the light guide 30 can be performed from a wavelength of a peak or a dip of an optical spectrum detected by the light detection unit 38, in other words, from the Bragg wavelength of the FBG sensor. Further, from amounts of wavelength shifts of peaks or dips of optical spectra detected by the light detection unit 38, in other words, from amounts of wavelength shifts of the Bragg wavelengths of the FBG sensors, a bend amount of the light guide 30 in that portion can be calculated. At this time, as a precondition, it is necessary that positions of the FBG sensors along the core can be specified from the wavelength order, that is, the lengths of the Bragg wavelengths of the FBG sensors would not be reversed even when the light guide 30 is largely bent.

A problem at this time is that if the bends of FBG sensors adjacent along the wavelength axis are large in mutually opposite directions, the order of the Bragg wavelengths of the FBG sensors may be reversed. Normally, in a use of a strain sensor that detects a local strain by using FBG sensors, in order to prevent such reversal, the sensor is designed in such a manner that a wavelength interval is widen more than twice the change in Bragg wavelength corresponding to an expected strain. According to this policy, it is necessary to separate adjacent FBG sensors more than twice the change in the Bragg wavelength of an FBG sensor corresponding to the minimum curvature radius of a measurement object whose bending is to be detected. In terms of pitch, it is necessary to separate adjacent FBG sensors more than twice the change in pitch corresponding to the change in Bragg wavelength.

However, since a normal continuous light source, tunable filter, and variable wavelength laser have limited wavelength bandwidth or wavelength sweep width, if the wavelength intervals are widen according to the above selecting manner of wavelength interval, there is a concern that the sufficient number of FBG sensors cannot be provided along the length of the light guide 30. In such a case, it would be necessary to use a broader band expensive light source, or to add a light source with higher or lower band, which leads to an increase in measurement cost.

(FBG Sensors in Each FBG Sensor Group have a Common Wavelength/Pitch)

The inventors of the present invention have devised the following configuration on the assumption of measuring a bend of a measurement object having a large diameter like a flexible insertion section of an endoscope. The light guide 30 is installed in a guide, such as a tube in an insertion section or on a side surface of an endoscope, so as to be freely deformable along the insertion section of the endoscope. It is preferable that the guide be on the axis of the insertion section of the endoscope, but it is not necessarily on the axis. Although the guide bends according to a bend of the insertion section of the endoscope, the guide has a structure with a margin so as not to hinder the movement of the light guide 30 in its axial direction and its twist direction.

In a measurement object with a large diameter, a bend would not drastically change unless being pressed from many lateral places.

Several FBG sensor groups among FBG sensor groups provided along a length of the light guide are arranged adjacently in the pitch space, and pitches of FBG sensors included in each of these FBG sensor groups are all coincident with one another. In other words, in the pitch space, pitches of FBG sensors included in each of FBG sensor groups included in a specific region are all the same. Thus, pairs, for example three pairs, of FBG sensors on the same core in two adjacent FBG sensor groups have the same pitch difference, and thus can be provided in common with the most appropriate pitch difference according to the position of the FBG sensor groups along the length of the light guide.

This contrivance is effective even when only performed on particular FBG sensor groups, and is particularly effective when performed on FBG sensor groups corresponding to a place where the minimum curvature radius of the measurement object is the smallest. Furthermore, if performed on all the FBG sensor groups, it is possible to narrow a necessary pitch band more effectively. An interval in the pitch space is preferably selected as narrow as possible and so that reversal of wavelengths will not occur, in consideration of the maximum curvature radius of a measurement object, a way to deform the measurement object, and relative positions and interval of FBG sensor groups with respect to the measurement object, etc. As a result, the pitch interval of the FBG sensors can be narrowed. Thus, it is possible to set many FBG sensors within a predetermined range in the pitch space while using the relatively inexpensive light source unit 12 (and the spectroscopic unit 14) having limited wavelength bandwidth or wavelength sweep width. Thereby, a curvature sensor of an inexpensive device configuration that performs bending measurement at many points is provided. Hereinafter, the number of FBG sensors that can be set within a predetermined range in the pitch space will be referred to as the pitch space utilization efficiency, for the sake of convenience.

Figure 11:
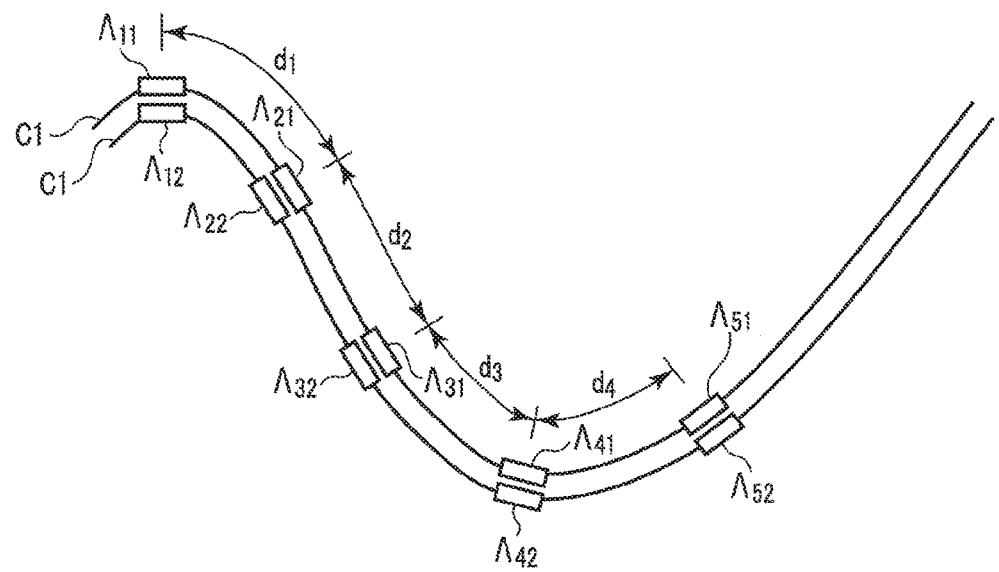
FIG. 11 shows two bent cores and FBG sensors provided on the cores.
Figure 12:
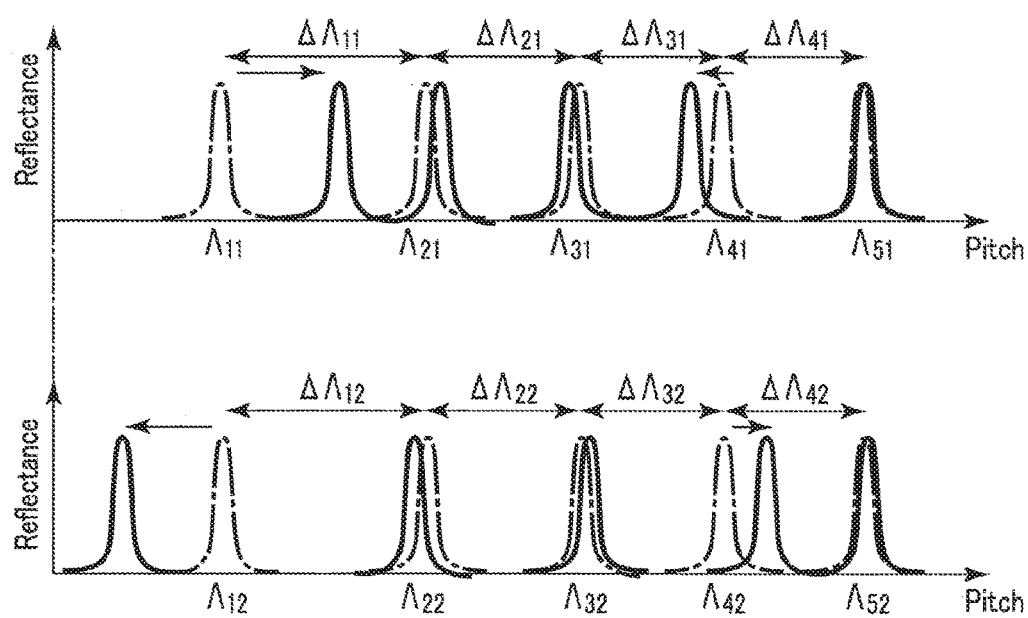
FIG. 12 shows a shift of a pitch along with bends of the cores.
Figure 13:
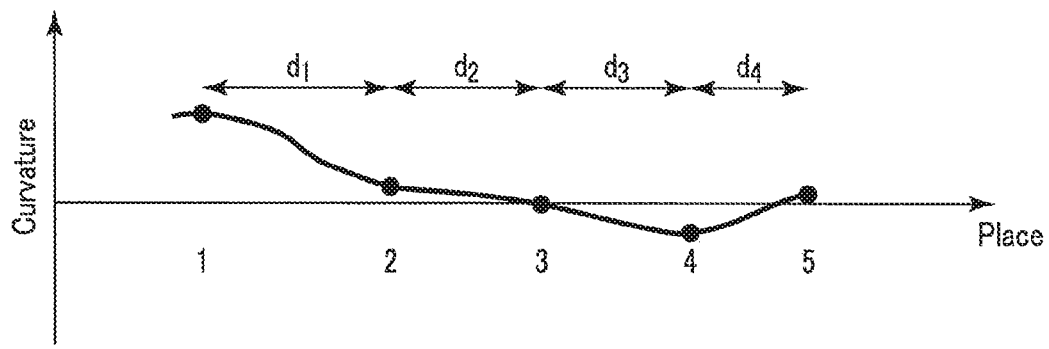
FIG. 13 shows a curvature of the cores at each position based on an interval of the FBG sensors shown in FIG. 11.

As shown in FIG. 11, FBG sensors arranged adjacently along the axes of the cores C1 and C2 are set to be arranged adjacently also in the pitch space, as shown in FIG. 12. In FIG. 11, reference symbols $\Lambda_{n1}$ and $\Lambda_{n2}$ (n is a natural number) respectively denote FBG sensors located on the cores C1 and C2, and also represent pitches of the FBG sensors. In addition, $d_n$ (n is a natural number) denotes an interval of two adjacent FBG sensor groups. In FIG. 12, a pitch of each FBG sensor in a state where the cores C1 and C2 are straight is indicated by a one-dot chain line, and a pitch after shifting due to the bending of the cores C1 and C2 as shown in FIG. 11 is indicated by a solid line. FIG. 13 shows curvatures of the cores C1 and C2 at respective positions based on the interval $d_n$ of the FBG sensors shown in FIG. 11. A curvature is a reciprocal of a curvature radius. As shown in FIG. 13, since the bending of the cores C1 and C2 would not largely change between the adjacent FBG sensors, unless a distance along the axes of the cores C1 and C2 is far apart, the interval can be set shorter than a pitch width corresponding to twice the minimum curvature radius of the measurement object.

As a result, for example, it is possible to arrange several tens of FBG sensors in an SLD that is a continuous light source having a small wavelength width of C-band (1530 nm to 1565 nm). Since the minimum curvature radius, 30 mm, of a colonoscope corresponds to a change (assuming that a core is offset by 50 μm with respect to a center axis of a fiber) in about 2.5 nm Bragg wavelength, only about seven points can be arranged in the normal standard, and the shape cannot be calculated with sufficient accuracy from the bending measurement. However, with the above-described contrivance, it is possible to secure 15 points or more of the number of points, and measurement of a sufficient number of points can be performed for a colonoscope of about 150 cm.

Figure 14:
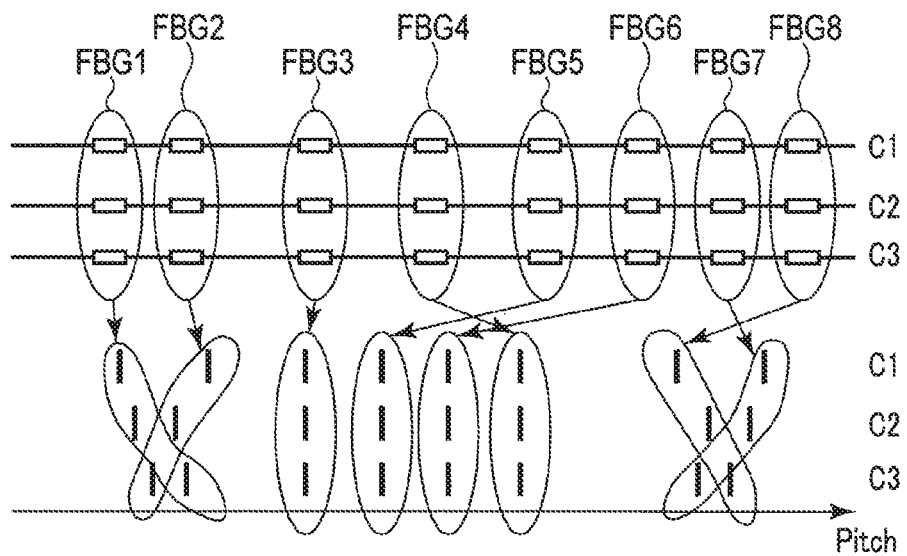
FIG. 14 shows an example of a positional relationship among the FBG sensor groups along a length of the cores and a relative relationship among pitches of the FBG sensors in each FBG sensor group in a pitch space.

FIGS. 14 and 15 show examples of FBG sensor groups according to the above-described contrivance. In FIGS. 14 and 15, a positional relationship of the FBG sensor groups along the lengths of the cores C1, C2, and C3 of the light guide 30 is shown in the upper row, and a relative relationship of pitches of FBG sensors in each FBG sensor group in the pitch space is shown in the lower row. Herein, explanation will be given by assuming that the number of FBG sensor groups provided in the light guide 30 is eight, for the sake of convenience. The eight FBG sensor groups are adjacent along the length of the light guide 30.

In an example shown in FIG. 14, several of the eight FBG sensor groups (FBG1 to FBG8), for example four FBG sensor groups (FBG3 to FBG6), are arranged adjacently in the pitch space. In addition to this, in FBG sensors included in each of these four FBG sensor groups (FBG3 to FBG6), their pitches in the pitch space are coincident with one another. In other words, pitches of all the FBG sensors included in each of the four FBG sensor groups (FBG3 to FBG6) included in a specific region in the pitch space are the same. Therefore, pairs, for example three pairs, of FBG sensors on the same core in two adjacent FBG sensor groups have the same pitch difference. Thus, the most appropriate pitch difference according to the positions of the FBG sensor groups along the length of the light guide can be provided for the pairs of FBG sensors in common. Thereby, the pitch space utilization efficiency can be maximized. In contrast, when the pitch difference is not the same, it is necessary to set with a margin so that reversal would not occur even when the pitch difference is the smallest, and thus the pitch space utilization efficiency cannot be maximized.

In an example shown in FIG. 15, all the eight FBG sensor groups (FBG1 to FBG8) are arranged adjacently in the pitch space. In addition to this, in FBG sensors included in each of all the eight FBG sensor groups (FBG1 to FBG8), their pitches in the pitch space are coincident with one another. That is, pitches of all the FBG sensors in each of all the eight FBG sensor groups (FBG1 to FBG8) are the same. Therefore, pairs, for example three pairs, of FBG sensors on the same core in two adjacent FBG sensor groups have the same pitch difference. Thus, the most appropriate pitch difference according to the positions of the FBG sensor groups along the length of the light guide can be provided for the pairs of FBG sensors in common. Thereby, the pitch space utilization efficiency can be maximized.

The examples shown in FIGS. 14 and 15 have eight FBG sensor groups, but may be generalized as follows, regardless of the number of the FBG sensor groups:

Several FBG sensor groups among FBG sensor groups provided along the length of the light guide are arranged adjacently in the pitch space, and pitches of FBG sensors included in each of these FBG sensor groups are all coincident with one another.

All the FBG sensor groups provided along the length of the light guide are arranged adjacently in the pitch space, and pitches of the FBG sensors included in each of these FBG sensor groups are all coincident with one another.

In the above description, a positional relationship of the FBG sensors in the FBG sensor groups adjacent along the length of the light guide 30 in the pitch space has been described. As described above, the pitch is related to the Bragg wavelength as $\lambda_B=2n\Lambda$. Therefore, if the effective refractive indices n of all the cores are the same, the pitch can be read as the Bragg wavelength. That is, the FBG sensor groups adjacent along the length of the light guide 30 are also adjacent in a wavelength space. Namely, two arranged FBG sensors on each core in two adjacent FBG sensor groups are adjacent in the wavelength space, and no other FBG sensor having a Bragg wavelength between Bragg wavelengths of the two FBG sensors exists.

The above-described generalized explanation of pitch may be modified as follows by reading pitch as Bragg wavelength.

Several FBG sensor groups among FBG sensor groups provided along the length of the light guide are arranged adjacently in the wavelength space, and in FBG sensors included in each of these FBG sensor groups, their Bragg wavelengths are coincident with one another.

All the FBG sensor groups provided along the length of the light guide are arranged adjacently in the wavelength space, and in the FBG sensors included in each of these FBG sensor groups, their Bragg wavelengths are coincident with one another.

Figure 16:
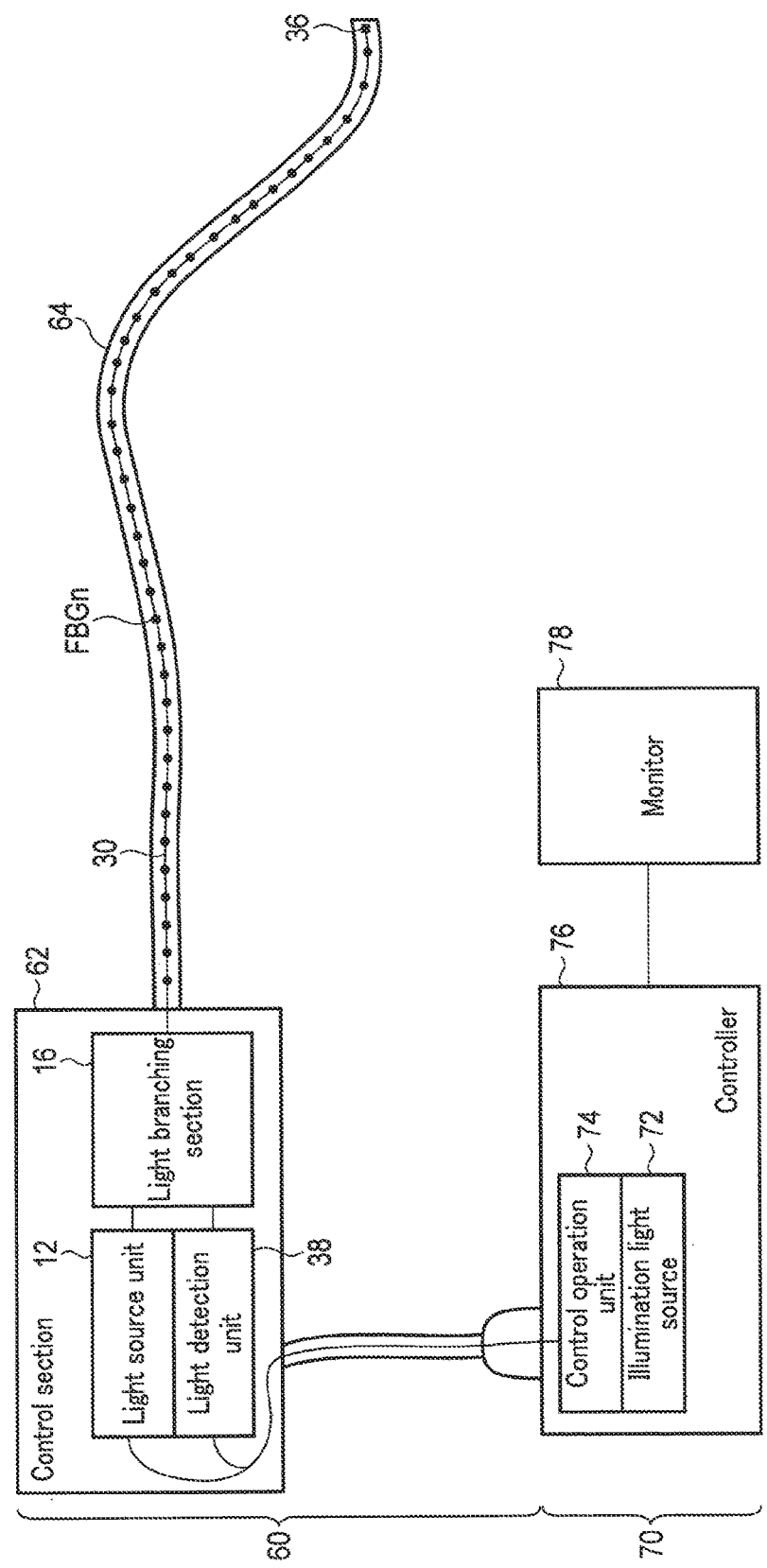
FIG. 16 shows an endoscope system into which the curvature sensor shown in FIG. 1 is incorporated.

FIG. 16 shows an endoscope system into which the curvature sensor of the present embodiment is incorporated. The endoscope system is divided into a scope 60 and a main body 70. The scope 60 has a bendable insertion section 64 into which an imaging device is incorporated at its tip end portion and a control section 62 that controls bending of the insertion section 64. The main body 70 comprises a controller 76 including a power supply, an illumination light source 72 for the scope, and a control operation unit 74 that performs controlling of the imaging device and operations such as image processing, and a monitor 78 that displays captured images and various kinds of information.

The scope 60 is attachable to and detachable from the main body 70, and is used by being exchanged with one having a different function (for examination, surgery, etc.) according to its use. Accordingly, common elements, such as the power supply, the illumination light source 72, and the control operation unit 74, are installed in the main body 70.

The light guide 30 of the curvature sensor is arranged along the length of the insertion section 64 of the scope 60 of the endoscope system. The light source unit 12, the light branching section 16, and the light detection unit 38 are arranged inside the control section 62 of the scope 60. In the example of FIG. 16, the light source unit 12 and the light detection unit 38 are both arranged inside the control section 62, but either one of the light source unit 12 and the light detection unit 38 may be installed inside the controller 76 of the main body 70.

In order to utilize an FBG sensor effectively, the light guide 30 is preferably a single mode fiber. Coupling of the single mode fiber requires special consideration, such as extremely precise positioning and no dust in a coupling part. Accordingly, the optical system of the curvature sensor is not installed on the side of the main body 70, which is routinely separated, but is installed in its entirety on the scope 60 side, so that stable performance can be obtained. Therefore, it is preferable that the electric system, such as the power supply and the controller 76, be on the main body 70 side, and the optical system, such as the light source unit 12 and the light detection unit 38, be on the scope 60 side. As a result, coupling (connector) related to the curvature sensor between the scope 60 and the main body 70 is constituted only by coupling of electric signals.

On the contrary, a configuration in which either one or both of the optical systems of the light source unit 12 and the light detection unit 38 are on the main body 70 side also has an advantage. While a single mode fiber coupler is required between the main body 70 and the scope 60, when the scope 60 is used by being exchanged with one having a different function (for examination, surgery, etc.), any one of or all of the optical systems (an SLD, a tunable filter, a detector, a fan-out part, etc.), such as the light source unit 12 and the light detection unit 38, can be shared. Thus, the cost of shape measurement can be suppressed.

(Rotation Prevention Mechanism)

In the curvature sensor, when the light guide 30 is twisted relative to the measurement object, the bend of the measurement object cannot be measured correctly, which leads to an error in calculation of the shape of the measurement object. Although the guide is contrived so as not to impair the movement of the light guide 30 in the twist direction as much as possible, when a bend is large, etc., the light guide 30 may be twisted due to friction between the light guide 30 and the guide. It is preferable to provide a rotation prevention mechanism that prevents rotation of the light guide 30 with respect to the measurement object.

Figure 17:
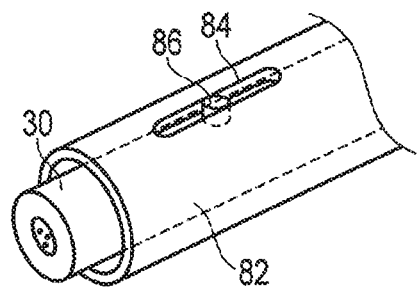
FIG. 17 shows an example of a rotation prevention mechanism.

In an example, as shown in FIG. 17, the rotation prevention mechanism may be constituted by a tubular guide 82 covering the periphery of the light guide 30 and having an elongated slit 84 extending along the length of the light guide 30 and a pin 86 extending from the light guide 30 to penetrate through the slit 84.

Figure 18:
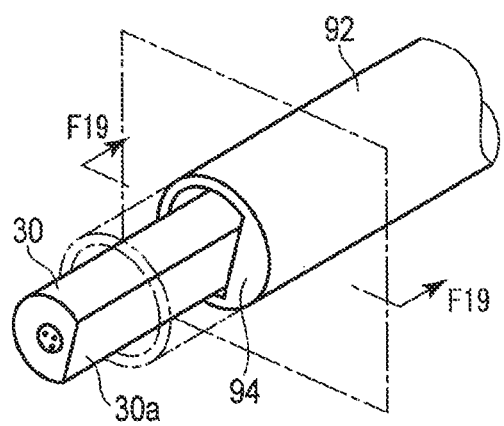
FIG. 18 shows another example of a rotation prevention mechanism.
Figure 19:
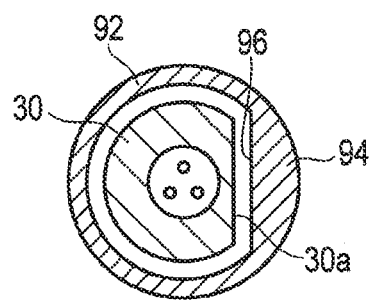
FIG. 19 shows a cross section taken along a line F19-F19 of FIG. 18.

In another example, as shown in FIGS. 18 and 19, the rotation prevention mechanism may have a flat portion 30a formed on a part of the light guide 30 and a tubular guide 92 covering the periphery of the light guide 30 and including a rotation stop 94 having a flat surface 96 facing the flat portion 30a.

Herein, the example in which the measurement object is an insertion section of a scope is presented, but other than this, the measurement object may be various probes, a catheter, and an oversheath (a tube for use in assisting insertion of an insertion section, a catheter, etc.).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A curvature sensor comprising:
a light source configured to emit light;
a flexible light guide comprising a plurality of cores disposed so as to maintain relative spaces, wherein the plurality of cores are configured to guide light emitted from the light source;
a plurality of fiber Bragg grating (FBG) sensors provided in the respective one of the plurality of cores of the flexible light guide and constitute FBG sensor groups at predetermined positions along longitudinal axes of the plurality of cores, respectively, wherein each of the plurality of FBG sensors comprises a grating having a predetermined pitch configured to reflect light with a particular wavelength corresponding to the predetermined pitch in light guided by the plurality of cores;
a detector configured to detect information on an optical spectrum of light reflected by the plurality of FBG sensors or light passing through the plurality of FBG sensors; and
a processor configured to determine a bend position and a bend amount of the flexible light guide based on the information on the optical spectrum,
wherein the FBG sensor groups positioned at the predetermined positions comprises a first FBG sensor group and a second FBG sensor group provided next to the first FBG sensor group in a longitudinal direction of the flexible light guide,
wherein all FBG sensors included in the first FBG sensor group each comprises a first grating having a predetermined first pitch,
wherein all FBG sensors included in the second FBG sensor group each comprises a second grating having a predetermined second pitch, the first pitch being shorter than the second pitch, and
wherein a difference between the first pitch and the second pitch is less than a difference between each of pitches of gratings of FBG sensors in all FBG sensor groups that include gratings having pitches shorter than the second pitch and the second pitch.

2. The curvature sensor according to claim 1, further comprising a light brancher that distributes light from the light source to the plurality of cores,
wherein the detector comprises sub-detectors configured to respectively detect light guided by the cores.

3. The curvature sensor according to claim 1,
wherein several FBG sensor groups among the FBG sensor groups are arranged adjacently in a wavelength space, and Bragg wavelengths of FBG sensors included in each of the FBG sensor groups are coincident with one another.

4. The curvature sensor according to claim 3,
wherein the FBG sensor groups are arranged adjacently in the wavelength space, and Bragg wavelengths of FBG sensors included in each of the FBG sensor groups are coincident with one another.

5. The curvature sensor according to claim 1,
wherein the flexible light guide is configured to be provided along a length of a bendable elongated object.

6. The curvature sensor according to claim 5,
wherein the plurality of cores extend along a length of the flexible light guide while maintaining relative spaces, and
wherein the curvature sensor further comprises a tubular guide covering a periphery of the flexible light guide, wherein the tubular guide is configured to abut against a surface of the flexible light guide to prevent rotation of the flexible light guide relative to the elongated object.

7. The curvature sensor according to claim 1,
wherein the flexible light guide is configured to be provided along a length of an insertion section of a scope of an endoscope system.

8. An endoscope system comprising:
a scope; and
the curvature sensor according to claim 1,
wherein either one of the light source and the detector is disposed inside the scope.

9. An endoscope system comprising:
a scope; and
the curvature sensor according to claim 1,
wherein the light source and the detector are disposed inside the scope.

* * * * *